United States Patent
Fabrizius et al.

(10) Patent No.: US 9,404,843 B2
(45) Date of Patent: Aug. 2, 2016

(54) SYSTEM AND METHOD FOR DETERMINING WEAR OF A WORN SURFACE

(71) Applicant: Caterpillar Inc., Peoria, IL (US)

(72) Inventors: Jacob P. Fabrizius, Corinth, MS (US); Trent A. Simpson, Peoria, IL (US); Robert E. Sharp, Corinth, MS (US); Benjamin J. Rasmussen, Sumter, SC (US); Jarrod D. Moss, Thomasville, GA (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 14/510,330

(22) Filed: Oct. 9, 2014

(65) Prior Publication Data

US 2016/0103050 A1    Apr. 14, 2016

(51) Int. Cl.
| | |
|---|---|
| *G01B 11/28* | (2006.01) |
| *G01N 3/56* | (2006.01) |
| *G01M 15/04* | (2006.01) |
| *G01B 11/22* | (2006.01) |

(52) U.S. Cl.
CPC *G01N 3/56* (2013.01); *G01B 11/22* (2013.01); *G01M 15/042* (2013.01)

(58) Field of Classification Search
CPC combination set(s) only.
See application file for complete search history.

(56) References Cited

U.S. PATENT DOCUMENTS

| | | | |
|---|---|---|---|
| 5,031,314 A | 7/1991 | Berrong et al. | |
| 6,701,615 B2 | 3/2004 | Harding et al. | |
| 7,012,701 B2 * | 3/2006 | Hassler | G01B 11/25 356/601 |
| 2005/0052657 A1 * | 3/2005 | Braghiroli | G01M 1/02 356/602 |
| 2006/0021870 A1 | 2/2006 | Tsai et al. | |
| 2006/0081459 A1 | 4/2006 | Tsai et al. | |

\* cited by examiner

*Primary Examiner* — Tri T Ton (57) ABSTRACT

A method of determining wear of a worn surface of a machine component includes providing a scanning device at a distance from the worn surface. The method also includes moving at least one of the scanning device and the worn surface relative to the other and generating a set of data points via the scanning device. Each data point of the set of data points is indicative of a depth of a corresponding point on the worn surface relative to a reference plane. The method further includes determining a maximum depth of the worn surface based on the set of data points and comparing the maximum depth to a reference value to determine a next step in a remanufacturing process of the machine component.

19 Claims, 5 Drawing Sheets

SYSTEM AND METHOD FOR DETERMINING WEAR OF A WORN SURFACE

TECHNICAL FIELD

The present disclosure generally relates to a system and a method for determining wear of a worn surface, and more particularly to a method of remanufacturing a machine component having a worn surface.

BACKGROUND

Typically components of a machine such as, an internal combustion engine, are subject to loads and abrasion during operation thereof. One such machine component, for example, is an engine block, which may experience loads from combustion events occurring within combustion chambers formed by the cylinder head, pistons, and cylinder bores of the engine block. These events may subject the engine block to loads and abrasion thereby causing wear on one or more surfaces of the engine block. Additionally, prolonged operation of the machine may also cause wear to one or more surfaces of the machine component.

These surfaces may be repaired or remanufactured using one or more machining processes to remove defects caused due to wear. For remanufacturing or repair purposes, one or more potential worn surfaces of the engine block may be inspected for defects. Moreover, a repair or remanufacturing process to be performed on the surfaces may vary based on an extent of wear. Conventional inspection methods may include visual inspection or other known means. However, these methods may not provide a precise measurement of an extent of wear of the surface.

Typically, an iterative process may be followed while remanufacturing the surfaces of the machine component. For example, after detecting defects on a surface, a machining operation may be performed in an attempt to remove the defects and then the surface is again inspected for defects. If the defects are still present, then the surface may be further machined. In some cases, machining the surface may result in a surface having size and/or dimensions beyond a print specifications originally defined for the surface. In such a case, a different remanufacturing process such as, a material deposition process may have to be performed. However, these processes may cause wastage of material. Moreover, a cycle of machining and inspecting until the defects are removed may have to be followed for multiple times which increases machine downtime.

For reference, U.S. patent publication No. 2006/021870 relates to a method of refurbishing a deposition target having a surface with an eroded region. The method involves measuring a depth profile of the eroded region. A target material is then provided to the eroded region in relation to the measured depth profile to refurbish the target by filling the eroded region with the target material.

SUMMARY OF THE DISCLOSURE

In one aspect of the present disclosure, a method of determining wear of a worn surface of a machine component is provided. The method includes providing a scanning device at a distance from the worn surface. The method also includes moving at least one of the scanning device and the worn surface relative to the other. The method further includes generating a set of data points via the scanning device. Each data point of the set of data points is indicative of a depth of a corresponding point on the worn surface relative to a reference plane. The method further includes determining a maximum depth of the worn surface based on the set of data points. The method also includes comparing the maximum depth to a reference value to determine a next step in a remanufacturing process of the machine component.

In another aspect of the present disclosure, a method of remanufacturing a machine component having a worn surface is provided. The method includes providing a scanning device at a distance from the worn surface. The method also includes moving at least one of the scanning device and the worn surface relative to the other. The method further includes generating a set of data points via the scanning device. Each data point of the set of data points is indicative of a depth of a corresponding point on the worn surface relative to a reference plane. The method further includes determining a maximum depth of the worn surface based on the set of data points. The method also includes comparing the maximum depth to a tolerance limit of the worn surface. The method further includes determining a remanufacturing operation to be performed on the worn surface based on the comparison.

In another aspect of the present disclosure, a system for determining wear of a worn surface of a machine component is provided. The system includes a support device, a scanning device and a controller. The support device is disposed adjacent to the worn surface. The support device includes an elongate member that is disposed at a distance relative to the worn surface. The scanning device is disposed on the elongate member of the support device and is configured to generate a set of data points. Each data point of the set of data points is indicative of a depth of a corresponding point on the worn surface relative to a reference plane. The controller is disposed in communication with the scanning device. The controller is configured to determine a maximum depth of the worn surface based on the set of data points. The controller is further configured to compare the maximum depth of the worn surface to a tolerance limit of the worn surface.

Other features and aspects of this disclosure will be apparent from the following description and the accompanying drawings.

DETAILED DESCRIPTION

Figure 1:
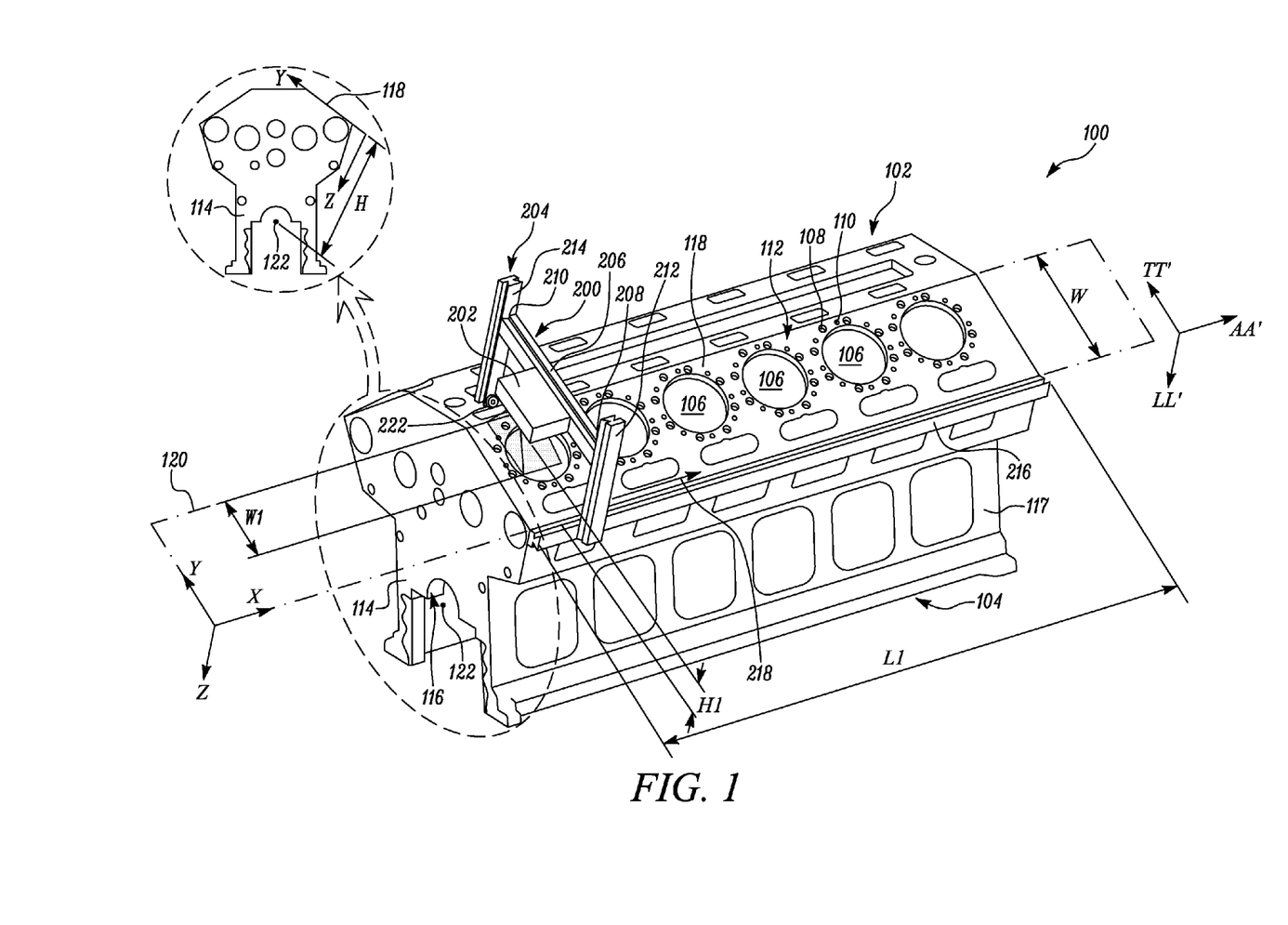
FIG. 1 is a perspective view of a scanning device being moved for a first pass over an exemplary machine component, according to an embodiment of the present disclosure.

Wherever possible, the same reference numbers will be used throughout the drawings to refer to same or like parts. FIG. 1 illustrates an exemplary machine component 100. The machine component 100 is embodied as an engine block. The machine component 100 may form part of an internal combustion engine (not shown) such as a compression ignition engine, a spark-ignition engine, or other combustion engines known in the art. Such an internal combustion engine, which includes the machine component 100, may be used to power various types of machines, such as, but not limited to, on-highway vehicles, off-highway vehicles, earthmoving machines, stationary equipment, or any other machines known in the art.

The machine component 100 may include an upper section 102 and a lower section 104. The upper section 102 of the machine component 100 may include a variety of openings, such as cylinder bores 106, attachment bores 108, and fluid passages 110. The cylinder bores 106 may be formed within the machine component 100 and open through a top deck 112 of the machine component 100. Each of the cylinder bores 106 may be configured to slidably receive a piston (not shown) therein. Although six cylinder bores 106 are shown, it should be appreciated that the machine component 100 may include any number of cylinder bores 106, each of which may or may not include a cylinder liner.

The fluid passages 110, such as coolant passages, may be circumferentially spaced about each cylinder bore 106. Each fluid passage 110 may be formed within the machine component 100 and may open through the top deck 112, as shown. The fluid passages 110 may be configured to provide cooling of the machine component 100, or components thereof.

A cylinder head (not shown) may be attached to the upper section 102 of the machine component 100 via, a plurality of attachment bolts (not shown) that may be threadably received within a corresponding number of the attachment bores 108. The cylinder head may enclose each of the cylinder bores 106, thus creating combustion chambers therein, and may provide a structure for supporting intake and exhaust valves and/or ports, fuel injectors, necessary linkages, and/or other known devices or structures.

The lower section 104 of the machine component 100 may include a crank case 114 defining a crank bore 116. The crank bore 116 may be configured to rotatably receive a crankshaft (not shown) therein. The machine component 100 may also include a side panel 117 that may enclose one or more components of the upper and/or lower sections 102, 104 of the machine component 100.

As shown in FIG. 1, the top deck 112 may be disposed at a height 'H' from a centre 'C' of the crank bore 116.

A person or ordinary skill in the art will acknowledge that the machine component 100, as shown in FIG. 1, is purely exemplary in nature and variations may be possible without deviating from the scope of the present disclosure. Further, various details of the machine component 100, such as, intake or exhaust ports, are not shown in FIG. 1 for illustrative purposes. Moreover, the machine component 100, as described above, may be used with any type and/or configuration of an internal combustion engine.

The internal combustion engine including the machine component 100 may experience loads due to combustion events occurring within the combustion chambers. In particular, during operation of the internal combustion engine, the machine component 100 may experience abrasion and loads due to vibrations, high temperature, and the like. Such loads and abrasion may result in erosion and/or wear within the machine component 100, particularly on the top deck 112.

Therefore, due to prolonged usage, a surface of the machine component 100 may undergo wear and/or erosion, thereby defining a worn surface 118. In the illustrated embodiment, the worn surface 118 is defined on the top deck 112. In various other embodiments, the worn surface 118 may be defined on other surfaces of the machine component 100, for example, lateral surfaces, surfaces of the cylinder bores 106 etc. The worn surface 118 may include one or more defects due to wear and/or erosion.

As shown in FIG. 1, the worn surface 118 may define a longitudinal axis AA' and a transverse axis TT'. The worn surface 118 may further define a lateral axis LL' that is perpendicular to both the longitudinal and transverse axes AA', TT'. The worn surface 118 may have a length 'L1' along the longitudinal axis AA' and, a width 'W' along the transverse axis TT'. The longitudinal, transverse and lateral axes AA', TT', LL' may be defined based on the original specifications of the machine component 100, specifically, the top deck 112. The original specifications of the machine component 100 may include dimensions, angles between various portions of the machine component 100 and other data related to the machine component 100 before sustaining any wear and/or erosion.

The machine component 100 may also define a reference plane 120 as shown in FIG. 1. The reference plane 120 may be indicative of a plane of the worn surface 118. The reference plane 120 may be indicated by two perpendicular axes X and Y. The reference plane 120 further defines a Z axis that is perpendicular to the reference plane 120. In an embodiment, the X, Y, Z axes may be same as the longitudinal, transverse and lateral axes AA', TT', LL' respectively.

In the illustrated embodiment, a position of the reference plane 120 may be determined by reference to a reference point 122 on the machine component 100. For example, the reference point 122 may be the centre 'C' of the crank bore 116. The height 'H' of the top deck 112 from the centre 'C' of the crank bore 116 may be determined. The height 'H' may be measured along a line parallel to the lateral axis LL'. Alternatively, the height 'H' may be acquired from original specifications of the machine component 100. As such, the reference plane 120 may lie at the height 'H' from the centre 'C' and perpendicular to the lateral axis LL'. However, in various embodiments, the reference plane 120 may be determined by reference to other reference points on the machine component 100.

In another embodiment, a position of the reference plane 120 may be determined from an original solid model of the machine component 100. The reference plane 120 may be determined as a plane of an original surface (the top deck 112 in the illustrated embodiment) which has undergone wear and resulted in the formation of the worn surface 118. Alternatively, other methods known to one of ordinary skill in the art may also be used to determine the reference plane 120.

For the purposes of remanufacturing, repair, and the like, the machine component 100 may be inspected to determine wear. As such, a remanufacturing operation that is to be performed on the machine component 100 may be determined based on the inspection. The present disclosure relates to a system 200 that may be employed to determine wear of a surface of a machine component 100. The system 200, which is employed to determine wear of the worn surface 118 of the machine component 100, will be described in detail hereinafter with reference to FIGS. 1 to 5.

Figure 2:
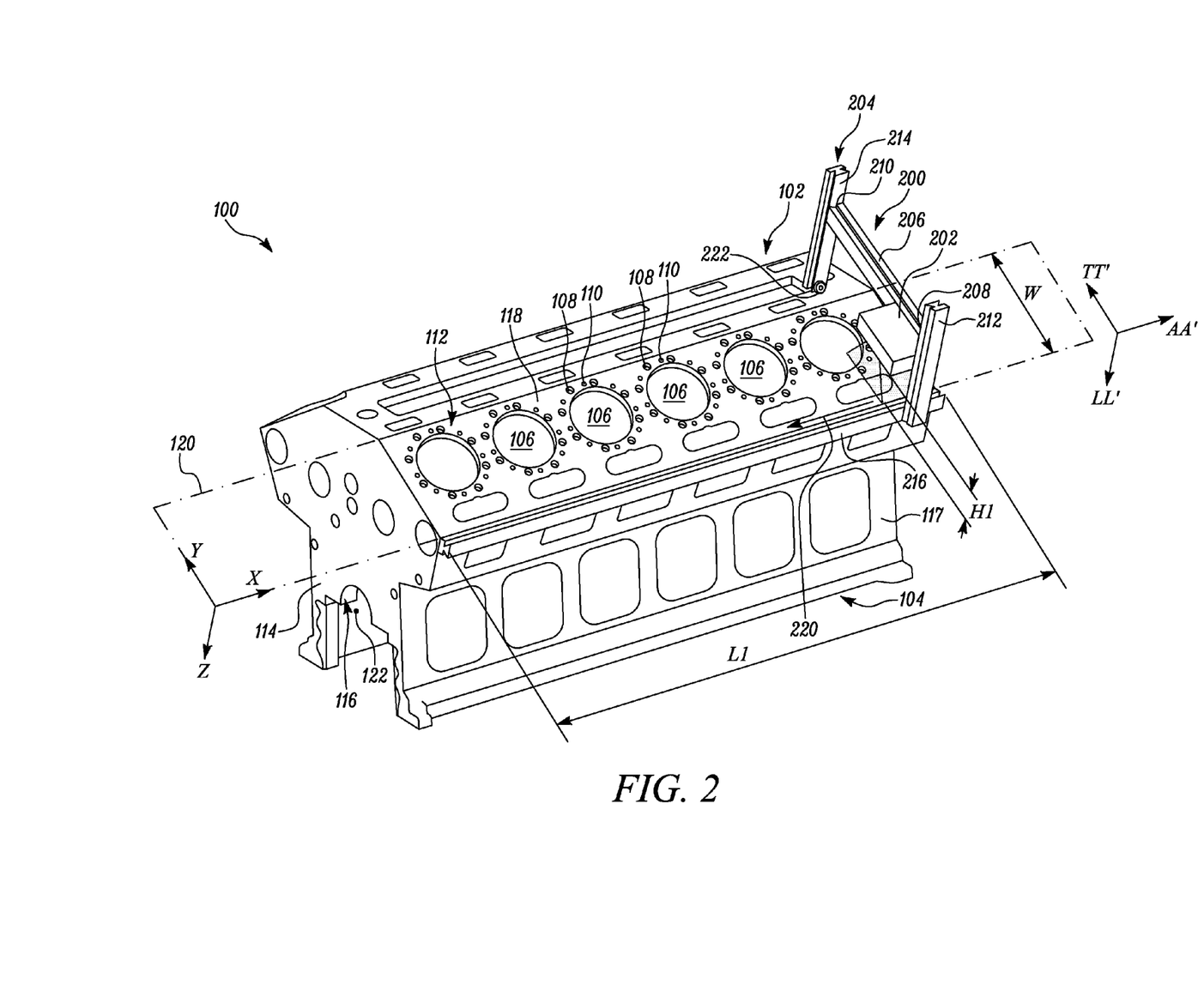
FIG. 2 is a perspective view of the scanning device being moved for a second pass over the machine component, according to an embodiment of the present disclosure.

Referring to FIGS. 1 and 2, the system 200 includes a scanning device 202 and a support device 204. The scanning device 202 may be configured to determine a positional data of a surface above which the scanning device 202 is positioned and/or moved. The positional data may be indicative of a shape and/or dimensions of the surface.

The scanning device 202 may include a scanning head (not shown) and, one or more sensors (not shown). The scanning head may include a radiation emitting member and an optical assembly. The radiation emitting member may be configured to emit radiation, such as, visible light, X-rays, ultrasound, laser, and the like, on the surface to be scanned. The optical assembly may include one or more lens and/or mirrors. The optical assembly may be configured to focus and/or deflect radiation that is reflected from the surface. The sensors may be configured to detect the reflected radiation and enable the scanning device 202 to determine the positional data based on the reflected radiation. The sensors may be one or more of a charge coupled device, a position sensitive device, and the like.

Accordingly, the scanning device 202 may be configured to allocate vector coordinates to every point on the surface based on the reflected radiation. The scanning device 202 may also include other components such as, but not limited to, input and/or output modules, control system, displays, etc., that may be configured to perform one or more functions of the scanning device 202. In an embodiment, the scanning device 202 may be a laser scanning device.

Alternatively, the scanning device 202 may not produce any radiation, but may be configured to detect ambient light reflected from the surface and determine positional data of the surface based on the reflected light.

In the illustrated embodiment, the scanning device 202 is provided at a distance 'H1' from the worn surface 118 and is configured to determine the positional data of the worn surface 118. Further, the scanning device 202 may be disposed on the support device 204. The support device 204 may be configured to hold and/or move the scanning device 202.

The support device 204 includes an elongate member 206 having a first end 208 and a second end 210. The elongate member 206 may have a length that is greater than or equal to the width 'W' of the worn surface 118 of the machine component 100. As shown in FIGS. 1 and 2, the elongate member 206 may be disposed at a distance relative to the worn surface 118. Moreover, the elongate member 206 may be disposed parallel to the transverse axis TT' of the worn surface 118.

As shown in FIGS. 1 and 2, the scanning device 202 is disposed on the elongate member 206. The scanning head of the scanning device 202 may face the worn surface 118. In the illustrated embodiment, the scanning device 202 may be movably mounted on the elongate member 206. For example, the scanning device 202 and the elongate member 206 may include a complementary rail and groove coupling such that the scanning device 202 may be slidable relative to the elongate member 206 along a length thereof. It may also be contemplated that the scanning device 202 may be rotatable relative to the elongate member 206. Further, the scanning device 202 may be removably coupled to the elongate member 206.

The elongate member 206 may also be configured to move parallel to the longitudinal axis AA' of the worn surface 118. In the illustrated embodiment, the support device 204 may include a first lateral member 212 and a second lateral member 214. The first and second lateral members 212, 214 may extend from the first and second ends 208, 210 of the elongate member 206, respectively, towards the worn surface 118. More specifically, the first and second lateral members 212, 214 may extend along the lateral axis LL'. The first and second lateral members 212, 214 may be configured to move along the longitudinal axis AA' of the worn surface 118.

In one embodiment, at least one of the first and second lateral members 212, 214 may be slidably coupled to a stationary member 216 of the support device 204. In the illustrated embodiment, the first lateral member 212 is slidably coupled to the stationary member 216. As shown in FIGS. 1 and 2, the stationary member 216 may be aligned parallel to the longitudinal axis AA' of the worn surface 118. Further, a rail and groove coupling may be provided between the first lateral member 212 and the stationary member 216 to enable a sliding movement of the first lateral member 212 relative to the stationary member 216. In an example, the stationary member 216 may be coupled to the side panel 117 of the machine component 100. Alternatively, the stationary member 216 may be mounted on external support members such as, a frame disposed adjacent to the machine component 100.

With such an arrangement, the elongate member 206 along with the first and second lateral members 212, 214 may move along the longitudinal axis AA'. One or more of the elongate member 206, the first lateral member 212 and the second lateral member 214 may be moved manually or automatically. A sliding motion of the first lateral member 212 relative to the stationary member 216 may enable the elongate member 206 along with the scanning device 202 to also move along the longitudinal axis AA'. The scanning device 202 may scan a width 'W1' of the worn surface 118 along the transverse axis TT' while moving along the longitudinal axis AA' in a first pass, as shown by an arrow 218 in FIG. 1. In the illustrated embodiment, the width 'W1' may be less than the width 'W' of the worn surface 118. The width 'W1' may depend on various parameters of the scanning device 202, for example, a type of laser, the optical assembly, the sensors, and the like. In an example, the width 'W1' may be adjustable. The scanning device 202 may be re-positioned on the elongate member 206. Thereafter, the scanning device 202 may be moved along the longitudinal axis AA' for a second pass, as shown by an arrow 220 in FIG. 2.

Although, in the present disclosure, the first pass and the second pass are explained, one of ordinary skill may recognize that any number of passes may be employed along the longitudinal axis AA' and/or the transverse axis LL' depending on the width 'W', the length 'L' of the worn surface 118. For example, if the width 'W' that is less than or equal to the width 'W1', the scanning device 202 may be moved along the longitudinal axis AA'. It is also understood that the scanning device 202 may be moved along the same path for multiple passes to enhance a precision of the positional data.

As shown in FIGS. 1 and 2, the support device 204 may also include a linear transducer 222. The linear transducer 222 may be disposed on the second lateral member 214 and may be configured to detect a position of the second lateral member 214 relative to the worn surface 118. As such, the position of the scanning device 202 may be determined. Alternatively, the scanning device 202 may have an integrated linear transducer 222 that is configured to detect the position of the scanning device 202.

The linear transducer 222 may include an encoder. The encoder may read a scale (not shown) and generate an analog or digital signal indicative of a position of the encoder with respect to the scale. The signal may be communicated to the scanning device 202 which may then decode the signal into a position. Therefore, while the scanning device 202 is moved along the worn surface 118 for a pass, the scanning device 202 may be able to determine a position thereof along the longitudinal axis AA' of the worn surface 118. Thus, the scanning device 202 may identify a location of a scanned portion of the worn surface 118 with respect to the X-axis of the reference plane 120. Further, overlaps between scanned portions along the X-axis may be avoided. In an example, the linear transducer 222 may be a hall effect sensor.

Figure 3:
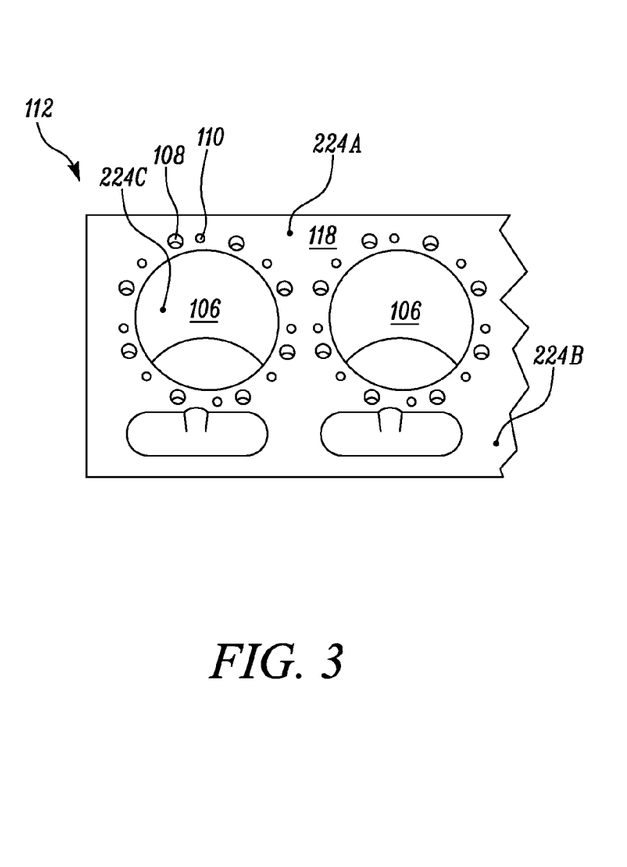
FIG. 3 is a partial perspective view of the worn surface of the machine component of FIG. 1.

FIG. 3 illustrates a partial perspective view of the worn surface 118 of the machine component 100 that is being scanned by the scanning device 202. The worn surface 118 may be defined by a set of points 224 (a first point 224A and a second point 224B are shown). The first point 224A and the second point 224B may have depths 'D1', 'D2' with respect to the reference plane 120. The scanning device 202 may be configured to determine a positional data of the set of points 224 on the worn surface 118 while moving along the worn surface 118.

Figure 4:
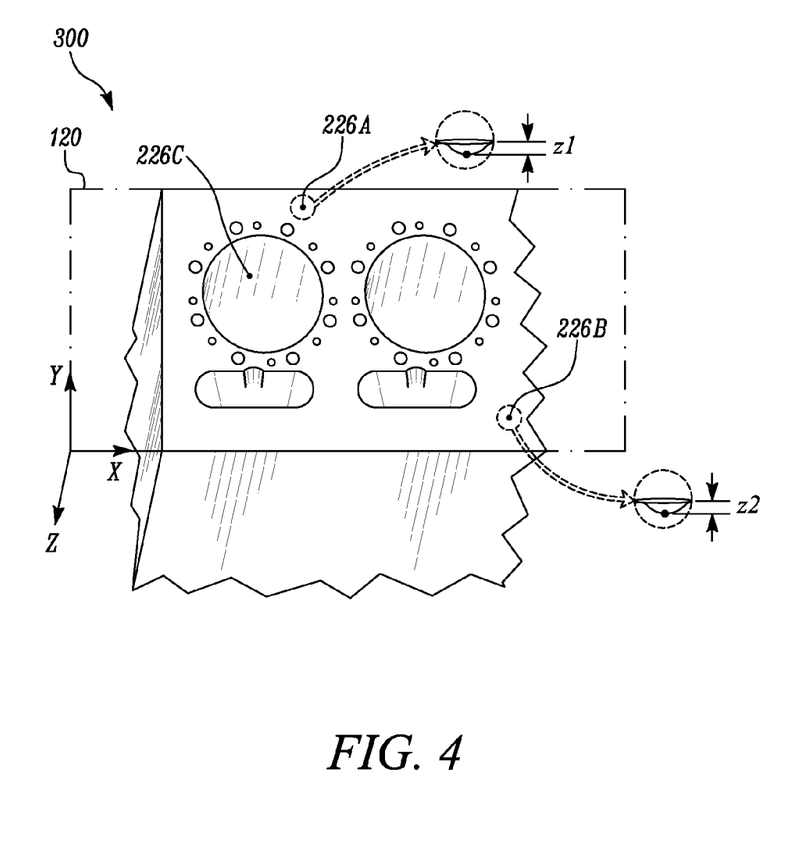
FIG. 4 is a perspective view of a three dimensional model of the worn surface of FIG. 3, according to an embodiment of the present disclosure.

FIG. 4 illustrates a three dimensional model 300 of the worn surface 118 shown in FIG. 3, according to an embodiment of the present disclosure. The scanning device 202 may generate the three dimensional model 300 with respect to the reference plane 120. The position of the reference plane 120 may be determined based on the methods described above. The reference plane 120 may be indicative of a plane of the worn surface 118. In an example, a position of the reference plane 120 may be manually entered into the scanning device 202. Alternatively, the scanning device 202 may determine the reference plane 120 based on the positional data of the set of points 224.

The scanning device 202 may be configured to generate a set of data points 226. In an embodiment, the scanning device 202 may generate the three dimensional model 300 of the worn surface 118 based on the set of data points 226. Each data point 226 of the set of data points 226 is indicative of a depth 'D' of a corresponding point 224 on the worn surface 118 relative to the reference plane 120. The depth 'D' may be measured along the Z-axis of the reference plane 120. In an embodiment, each data point 226 may also indicate a position of the corresponding point 224 on a plane of the worn surface 118. For example, each data point 226 may be indicated by three coordinates (x, y, z). The (x, y) coordinates of each data point 226 may indicate a position of the corresponding points 224 of the worn surface 118 in the reference plane 120. The 'z' coordinate of the data point 226 may indicate the depth 'D' of corresponding points of the worn surface 118 measured from the reference plane 120 along the Z-axis. It may be apparent that the 'z' coordinate of one or more data points 226 may be zero if the corresponding depth 'D' of the point 224 is zero. Further, a zero value of the 'z' coordinate may be indicative of zero wear on the corresponding point 224.

For example, the first point 224A and the second point 224B on the worn surface 118 shown in FIG. 3 may be indicated by the first data point 226A and the second data point 226B shown in FIG. 4. The first and second data points 226A, 226B may have coordinates (x1, y1, z1) and (x2, y2, z2) respectively. Accordingly, the depths 'D1', 'D2' of the first point 224A and the second point 224B relative to the reference plane 120 may be represented by the z-coordinates of the first and second data points 226A, 226B respectively. Similarly, all the points on the worn surface 118 are represented by the set of data points 226 indicating corresponding depths.

Alternatively, the set of data points 226 may have a single coordinate that indicates a depth of a corresponding point on the worn surface 118 relative to the reference plane 120. In such a case, the scanning device 202 may generate an array including positional data indicative of the depths of the corresponding points on the worn surface 118 instead of generating the three dimensional model 300. It may also be contemplated that the scanning device 202 may generate an array of data points having all the three coordinates and may optionally generate the three dimensional model 300.

Figure 5:
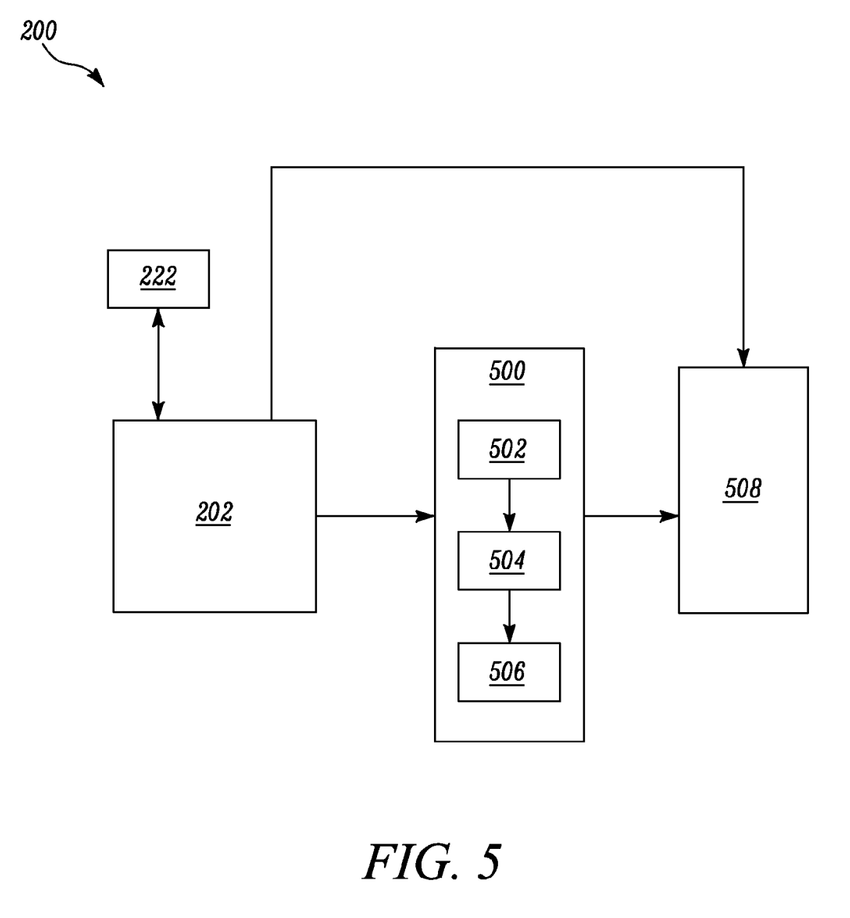
FIG. 5 is a block diagram of a system for detecting wear of a worn surface of a machine component, according to an embodiment of the present disclosure.

Referring now to FIG. 5, a block diagram of the system 200 is illustrated. The system 200 includes a controller 500 disposed in communication with the scanning device 202. The controller 500 may embody a CPU, a microprocessor, a microcontroller, a PLC or other device. The controller 500 may be configured to receive signals from various components within the controller 500 and/or other devices such as, the scanning device 202. The controller 500 may also include one or more input and output modules for receiving and transferring data. The controller 500 may also be configured to receive manual inputs. The controller 500 may also include an associated memory, or a database that may store the information processed by the controller 500 or received from other sources.

It should be appreciated that the controller 500 may also embody a machine microprocessor capable of controlling numerous machine functions. A person of ordinary skill in the art will appreciate that the controller 500 may additionally include other components and may also perform other functions not described herein.

In the illustrated embodiment, the controller 500 is disposed in communication with the scanning device 202. The controller 500 may be configured to control and operate the scanning device 202. The controller 500 may also receive and process information generated by the scanning device 202. Particularly, the controller 500 may be configured to receive the set of data points 226 and the three dimensional model 300 from the scanning device 202. The controller 500 may be configured to determine a maximum depth 'Dm' of the worn surface 118 based on the set of data points 226. The controller 500 may be further configured to compare the maximum depth 'Dm' to a reference value 'R' to determine a next step in a remanufacturing process of the machine component 100.

Accordingly, the controller 500 may include a first module 502, a second module 504 and a third module 506. The first module 502 may be configured to remove one or more data points from the set of data points 226 that have a depth 'D' greater than a predetermined threshold limit 'L0'. The threshold limit 'L0' may depend on a shape and/or dimensions of holes, chamfers and other design features provided on the worn surface 118. Such design features may be part of the original top deck 112 and may be unrelated to any wear and/or erosion. The threshold limit 'L0' may also depend on a maximum limit of wear that may occur in the worn surface 118. As such, the first module 502 may remove the data points 226 corresponding to the points 224 on walls surrounding the holes, chamfers and the like. In the illustrated embodiment, the controller 500 may remove the data points corresponding to walls surrounding the cylinder bores 106 and the fluid passages 110. Hence, the first module 502 may store the set of data points 226 that do not include the data points having a depth greater than the predetermined threshold limit 'L0'. For example, the first module 502 may remove the data point 226C corresponding to the third point 224C on a wall of the cylinder bore 106 from the set of data points 226.

In one embodiment, the set of data points 226 may not contain data points 226 that have a depth 'D' greater than the predetermined threshold limit 'L0'. In such a case, the first module 502 may store the set of data points 226 received from the scanning device 202 without any modification.

The second module 504 may receive the stored set of data points 226 from the first module 502. The second module 504 may be configured to determine the maximum depth 'Dm' of the worn surface 118 based on the set of data points 226. The second module 504 may compare the depths 'D' indicated by the set of data points 226 and output the maximum depth 'Dm'. The second module 504 may suitably employ known algorithms to determine the maximum depth 'Dm'. The maximum depth 'Dm' may indicate an extent of wear present on the worn surface 118. Additionally or optionally, the second module 504 may also output the data point corresponding to the maximum depth 'Dm'.

In an embodiment, at least one of the controller 500 or the scanning device 202 may segment the worn surface 118 based on a user input or pre-stored information. Further, the second module 504 may determine maximum depths 'Dm' for each of the segments of the worn surface 118.

The third module 506 may receive the maximum depth 'Dm' determined by the second module 504. The third module 506 of the controller 500 may be further configured to compare the maximum depth 'Dm' to a reference value 'R' to determine a next step in a remanufacturing process of the machine component 100. In one embodiment, the reference value 'R' may be a tolerance limit 'R0' of the worn surface 118. The reference value 'R' may be stored in the memory or the database associated with the controller 500. Alternatively, the reference value 'R' may be entered manually. The third module 506 may return a first value 'V1' if the maximum depth 'Dm' is less than the tolerance limit 'R0'. Further, the third module 506 may return a second value 'V2' if the maximum depth 'Dm' is greater than or equal to the reference value 'R'. The first and second values 'V1', 'V2' may be for example, 0 and 1, respectively.

The controller 500 may be further configured to determine a next step in a remanufacturing process of the machine component 100 based on the first and second values 'V1', 'V2'. In an embodiment, the controller 500 may determine a next step as a first process if the maximum depth 'Dm' is less than the reference value 'R', i.e., upon receiving the first value 'V1'. The first process may include machining the worn surface 118 within the tolerance limit 'R0' of the worn surface 118.

The controller 500 may determine a next step in a remanufacturing process as a second process to be performed on the worn surface 118 if the maximum depth 'Dm' is greater than or equal to the tolerance limit 'R0', i.e., upon receiving the second value 'V2'. The second process includes machining the worn surface 118 beyond the tolerance limit 'R0'. The second process may also include performing a material deposition operation on the machined surface.

In another embodiment, the controller 500 may compare the maximum depth 'Dm' of each segment of the worn surface 118 to the tolerance limit 'R0'. In such a case, the controller 500 may determine a different process for each of the segments.

Still referring to FIG. 5, the system 200 may also include a display device 508. The display device 508 may be communicably coupled to the scanning device 202 and the controller 500. The display device 508 may be configured to allow visualization of the information processed by the controller 500 and the scanning device 202. In an example, the display device 508 may show an image of the three dimensional model 300. The image may be displayed in a graphical user interface (GUI) to enable a user to interact and manipulate the image. For example, a user may be able to move and/or rotate the image of the three dimensional model 300. The user may also be able to view the coordinates of various data points 226 by moving a pointer (for example, a cursor) on corresponding locations on the image. Further, the user may also be able to zoom in and zoom out the image to see details such as, wear and the like. The display device 508 may be further configured to display the maximum depth 'Dm', and the remanufacturing process determined by the controller 500.

Although the system 200 is explained in conjunction with the machine component 100, one of ordinary skill in the art will acknowledge that embodiments of the present disclosure may be similarly applied to or implemented with any other machine component having a worn surface. In an example, the system 200 may be suitably employed to determine wear of one or more components of a pump.

Figure 6:
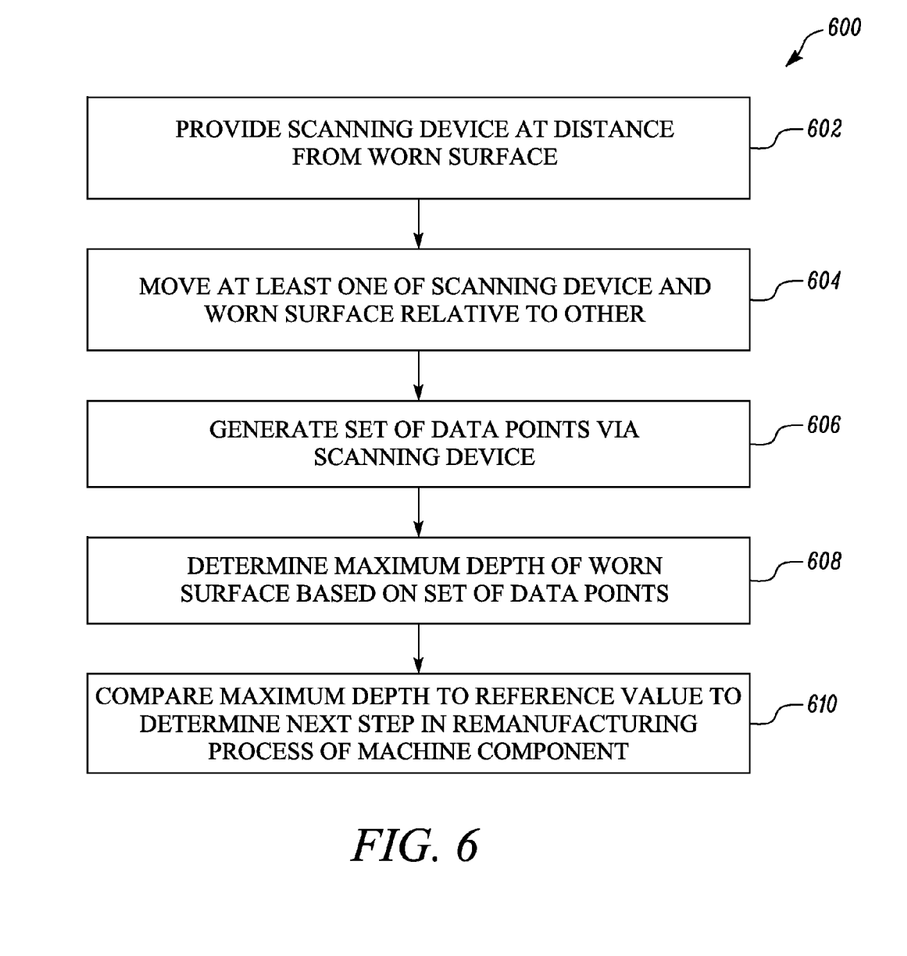
FIG. 6 is a flowchart of a method for detecting wear of a worn surface of a machine component, according to an embodiment of the present disclosure.

Referring to FIG. 6, a method 600 of detecting wear of a worn surface of a machine component is illustrated, according to an embodiment of the present disclosure. The method 600 will be explained in relation to the worn surface 118 of the machine component 100 illustrated in FIG. 1. However, it may be envisioned to suitably implement the method 600 to detect wear of any worn surface which may be part of various other machine components. In an embodiment, the system 200 may be employed to implement one or more steps of the method 600 as will be explained herein.

At step 602, the method 600 includes providing the scanning device 202 at the distance 'H1' from the worn surface 118. The distance 'H1' may depend on a type of the scanning device 202. In an example, if the scanning device 202 is a measuring probe of a coordinate measuring machine (CMM), the distance 'H1' may be approximately equal to zero. In such a case, the scanning device 202 may contact the worn surface 118. In another example, if the scanning device 202 is a laser scanning device, the distance 'H1' may be a nonzero value. In the illustrated embodiment, the scanning device 202 may be disposed on the elongate member 206 of the support device 204 in order to position the scanning device 202 at the distance 'H1' above the worn surface 118.

At step 604, the method 600 includes moving at least one of the scanning device 202 and the worn surface 118 relative to the other. Specifically, the method 600 may include moving at least one of the scanning device 202 and the worn surface 118 along at least one of the longitudinal axis AA' and the transverse axis TT'. Further, moving at least one of the scanning device 202 and the worn surface 118 may also include rotating at least one of the scanning device 202 and the worn surface 118 about an axis.

In the illustrated embodiment, the scanning device 202 may be moved along at least one of the longitudinal axis AA' and the transverse axis TT'. Referring to FIGS. 1 and 2, the scanning device 202 may be disposed on the elongate member 206 that is configured to move along with the first lateral member 212. The first lateral member 212 may be slidably coupled to the stationary member 216. As such, by sliding the first lateral member 212, the scanning device 202 may be moved along the longitudinal axis AA'. Moreover, the scanning device 202 may also be moved along the transverse axis TT' that is perpendicular to the longitudinal axis AA'.

As shown in FIGS. 1 and 2, the scanning device 202 may be moved for the first pass and the second pass respectively. Moreover, the scanning device 202 may be moved for one or more passes along the longitudinal axis AA' and/or the transverse axis TT' depending on the scanning width 'W1' of the scanning device 202, and the width 'W', the length 'L' of the worn surface 118.

In an embodiment, the method 600 may include utilizing multiple scanning devices 202 to determine positional data of the worn surface 118. As such, each of the scanning devices 202 may be moved relative to the worn surface 118 for respective passes.

A person of ordinary skill in the art will acknowledge that the support device 204 described herein is exemplary and non-limiting of this disclosure. It may be contemplated to modify the support device 204 by adding and/or removing one or more components of the support device 204 depending on a shape and/or dimensions of the worn surface 118 and the machine component 100.

In one example, an operator may hold the scanning device 202 at the required distance 'H1' and also move the scanning device 202. In another example, the scanning device 202 may be hung from an overhead structure via a support member. The support member may be configured to move along a rail of the overhead structure thereby moving the scanning device 202 along the required direction. In yet another example, the scanning device 202 may be mounted on a robotic arm that may be movable along one or more axes of the worn surface 118.

Although the scanning device 202 is shown to be movable relative to the worn surface 118 and the machine component 100 is kept stationary, it may also be contemplated that the machine component 100 may be moved relative to the scanning device 202. For example, the machine component 100 may be moved along at least one of the longitudinal axis AA' and the transverse axis TT'. In such a case, the scanning device 202 may be disposed on a fixed support or a movable support.

The worn surface 118, as described above, may be substantially planar. However, the system 200 and the method 600 may also be used for determining wear of a non-planar surface. For example, the worn surface may be defined on a non-planar surface such as, an inner diameter of each of the cylinder bores 106 or an outer diameter of a cylinder liner. In case of the cylinder bores 106, the machine component 100 and/or the scanning device 202 may be configured to rotate about the lateral axis LL' axis defined by the non-planar surface. Additionally, the scanning device 202 and/or the machine component 100 may also be linearly moved along at least one of the longitudinal axis AA' or the transverse axis TT'. A support device for the scanning device 202 may vary accordingly.

At step 606, the method 600 includes generating the set of data points 226 via the scanning device 202. Each of the data points 226 may be indicative of the depth 'D' of the corresponding point 224 on the worn surface 118 relative to the reference plane 120. At step 606, the method 600 may also include determining a position of the reference plane 120. In one embodiment, the position of the reference plane 120 may be determined by reference to the reference point 122 on the machine component 100. The position of the reference plane 120 may vary based on a location of the worn surface 118 on the machine component 100. In the illustrated embodiment, the position of the reference plane 120 may be determined by reference to the centre of the crank bore 116. Referring to FIGS. 3 and 4, the first and second data points 226A, 226B may indicate the depths z1 and z2 relative to the reference plane 120 for the corresponding first and second points 224A, 224B on the worn surface 118. Similarly, all the points on the worn surface 118 may be represented by the set of data points 226 indicating corresponding depths.

The scanning device 202 as described above may generate the set of data points 226 relative to the reference plane 120 associated with the machine component 100. However, it may also be contemplated that the scanning device 202 may generate the set of data points 226 with respect to various other reference frames. In an example, the scanning device 202 may generate the set of data points 226 with respect to a reference frame associated with a support structure on which the scanning device 202 is mounted. The support structure may be for example, a spindle of a computer numerical control (CNC) machine, a robotic arm, a co-ordinate measuring machine etc.

In an embodiment, for a non-planar worn surface, such as the cylinder bores 106 and cylinder liners, the scanning device 202 may be configured to generate the set of data points 226 with respect to a suitable co-ordinate system such as a cylindrical co-ordinate system.

At step 608, the method 600 includes determining the maximum depth 'Dm' of the worn surface 118 based on the set of data points 226. In an embodiment, the maximum depth 'Dm' may be determined by the controller 500 that is in communication with the scanning device 202. As described earlier herein, the second module 504 of the controller 500 may compare the depths 'D' indicated by the set of data points 226 and output the maximum depth 'Dm'. Additionally or optionally, the controller 500 may also output the data point corresponding to the maximum depth 'Dm'. The maximum depth 'Dm' may indicate a maximum extent of wear present on the worn surface 118.

In an embodiment, the controller 500 may also be configured to segment the worn surface 118 based on a user input or a previously stored information. With such a configuration, the controller 500 may be additionally configured to determine the maximum depth 'Dm' for each of the segments of the worn surface 118.

Moreover, the first module 502 of the controller 500 may remove one or more data points from the set of data points 226 that have a depth 'D' greater than the predetermined threshold limit 'L0'. The threshold limit 'L0' may depend on a shape and/or sizes of holes, chamfers and other unrelated design features provided on the worn surface 118. The threshold limit 'L0' may also depend on a maximum limit of wear that may occur in the worn surface 118.

With such a configuration, the second module 504 of the controller 500 may analyze only the set of data points 226 corresponding to the points 224 on the worn surface 118. Therefore, the second module 504 may not determine the maximum depth 'Dm' to be the depth indicated by the data points 226 corresponding to the cylinder bores 106, the fluid passages 110, chamfers or other unrelated design features of the worn surface 118.

At step 610, the method 600 includes comparing the maximum depth 'Dm' to the reference value 'R' to determine a next step in a remanufacturing process of the machine component 100. In one embodiment, the third module 506 of the controller 500 may be configured to compare the maximum depth 'Dm' to the reference value 'R'. The reference value 'R' may be the tolerance limit 'R0' of the worn surface 118. The tolerance limit 'R0' may depend on the print specifications for the machine component 100. As such, by comparing the maximum depth 'Dm' to the tolerance limit 'R0', one may conveniently establish a remanufacturing process to be performed on the worn surface 118. For example, if the maximum depth 'Dm' is less than the tolerance limit 'R0', a machining process within the tolerance limit 'R0' may be performed. Alternatively, the reference value 'R' may be selected to indicate other limitations upon which various analyses may be performed.

The controller 500 may determine a next step in a remanufacturing process of the machine component 100 as the first process if the maximum depth 'Dm' is less than the tolerance limit 'R0'. The first process may include machining the worn surface 118 within the tolerance limit 'R0' of the worn surface 118. Specifically, a depth of machining may be kept within the tolerance limit 'R0'. Thus, the first process may include removing the material from the worn surface 118 so as to obtain a uniform depth of the worn surface 118 within the tolerance limit 'R0' relative to the reference plane 120.

The controller 500 may determine a next step in a remanufacturing process as the second process to be performed on the worn surface 118 if the maximum depth 'Dm' is greater than or equal to the tolerance limit 'R0'. The second process may include machining the worn surface 118 beyond the tolerance limit 'R0'. The second process may also include performing a material deposition operation on the machined surface. The material may be deposited on the worn surface 118 so as to obtain a uniform depth of the worn surface 118 that may be less than the tolerance limit 'R0' relative to the reference plane 120.

In an embodiment, the method 600 may also be implemented for detecting wears of multiple segments of the worn surface 118. The controller 500 may compare the maximum depth 'Dm' of each segment of the worn surface 118 to the tolerance limit 'R0'. In such a case, the controller 500 may determine a different process for each of the segments. Further, it may also be contemplated to implement the method 600 for detecting wear of multiple machine components. For example, multiple cylinder heads may be mounted on a fixture of a machine table and the scanning device 202 may be moved relative to each of the cylinder heads. The controller 500 may compare the maximum depth determined for each cylinder head to respective tolerance limits. Further, the controller 500 may determine a different remanufacturing process for each of the cylinder heads based on the comparison.

The machining of the worn surface 118 may be accomplished using any known machining process, such as, milling, turning, grinding, or a combination thereof. The process can be manual and/or automatic. For example, a machining tool may be used to remove material from the worn surface 118 that may be operated via computer numerical control (CNC). Moreover, the scanning device 202 may be mounted on the spindle of the CNC machine and the controller 500 of the system 200 may directly communicate data, such as the maximum depth 'Dm' and the remanufacturing process to be performed, to the CNC machine. The material deposition may be performed by any known methods known in the art such as, but not limited to, plasma deposition, electron beam powder deposition, laser powder deposition, wire deposition process, and the like.

Although the method 600 is explained in conjunction with the machine component 100 and the worn surface 118 defined on the top deck 112, one of ordinary skill in the art will acknowledge that embodiments of the present disclosure may be similarly applied to or implemented in any other machine component having one or more worn surfaces.

INDUSTRIAL APPLICABILITY

The present disclosure has applicability in inspection, remanufacture or repair of a machine component having a worn surface. Moreover, such tasks may be accomplished using the system 200 described herein. Embodiments of the present disclosure may enable determination of wear of the worn surface 118.

The present disclosure is also related to the method 600. The method 600 may provide accurate determination of wear occurring on a surface of a machine component. Moreover, the maximum depth 'Dm' may be determined accurately with minimum manual intervention. Additionally, the data from the controller 500 and the scanning device 202 may be communicated to a Computer Numeric Control (CNC) machine for automating a subsequent machining process.

The present disclosure also relates to a method of remanufacturing a machine component 100 having a worn surface 118. The method includes determining wear of the worn surface 118 by implementing steps of the method 600. With such an implementation, an extent of wear of the worn surface 118 may be determined. More specifically, a manufacturer may determine whether the extent of wear is within the tolerance limit 'R0' or more than the tolerance limit 'R0'. Accordingly, a next step in a remanufacturing process may be determined. It may also be contemplated that the system 200 and the method 600 may be used during manufacturing of a machine component for accurately detecting any manufacturing defect.

Moreover, an amount of material or a thickness of material to be removed from the worn surface 118 may be also be determined based on the comparison between the maximum depth 'Dm' and the tolerance limit 'R0'. Further, an amount of material that is to be deposited on the machined surface may also be determined. Therefore, multiple cycle times associated with repetitive inspection and machining may be minimized. For example, measuring a height of the top deck 112 repeatedly, after each machining step, to determine if a height of the worn surface 118 is within the print specifications of the machine component 100 may be avoided.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A method of determining wear of a worn surface of an engine using a wear detection system, the wear detection system including a support device disposed adjacent to the worn surface, the support device comprising an elongate member disposed at a distance relative to the worn surface, wherein the elongate member is movable relative to the worn surface; a scanning device disposed on the elongate member of the support device, the scanning device configured to generate a set of data points, wherein each data point of the set of data points is indicative of a depth of a corresponding point on the worn surface relative to a reference plane; and a controller disposed in communication with the scanning device, the controller configured to determine a maximum depth of the worn surface based on the set of data points and compare the maximum depth of the worn surface to a reference value of the worn surface, the method comprising:
    moving at least one of the scanning device and the worn surface relative to the other;
    generating the set of data points via the scanning device, wherein each data point of the set of data points is indicative of the depth of the corresponding point on the worn surface relative to the reference plane;
    determining the maximum depth of the worn surface based on the set of data points;
    comparing the maximum depth to the reference value to determine a next step in a remanufacturing process of the engine;
    machining the worn surface beyond the reference value of the worn surface if the maximum depth is greater than the reference value; and
    performing a material deposition operation on the machined surface.

2. The method of claim 1, wherein the worn surface defines a longitudinal axis and a transverse axis perpendicular to the longitudinal axis, and wherein the scanning device is moved along at least one of the longitudinal axis and the transverse axis.

3. The method of claim 1 further comprising removing a data point from the set of data points indicative of a depth greater than a predetermined threshold limit.

4. The method of claim 1, wherein the reference value is a tolerance limit of the worn surface.

5. The method of claim 1, wherein each data point of the set of data points is further indicative of a position of the corresponding point on a plane of the worn surface.

6. The method of claim 1 further comprising determining the position of the reference plane by reference to a reference point on the engine.

7. The method of claim 1 further comprising generating a three dimensional model of the worn surface based on the set of data points.

8. The method of claim 1 further comprising, monitoring via a linear transducer, a position of the scanning device relative to the worn surface.

9. The method of claim 1, wherein the step of moving at least one of the scanning device and the worn surface includes rotating at least one of the scanning device and the worn surface about an axis.

10. A method of remanufacturing an engine having a worn surface using, in part a wear detection system, the wear detection system including a support device disposed adjacent to the worn surface, the support device comprising an elongate member disposed at a distance relative to the worn surface, wherein the elongate member is movable relative to the worn surface; a scanning device disposed on the elongate member of the support device, the scanning device configured to generate a set of data points, wherein each data point of the set of data points is indicative of a depth of a corresponding point on the worn surface relative to a reference plane; and a controller disposed in communication with the scanning device, the controller configured to determine a maximum depth of the worn surface based on the set of data points and compare the maximum depth of the worn surface to a tolerance limit of the worn surface, the method comprising:

moving at least one of the scanning device and the worn surface relative to the other;

generating the set of data points via the scanning device, wherein each data point of the set of data points is indicative of the depth of the corresponding point on the worn surface relative to the reference plane;

determining the maximum depth of the worn surface based on the set of data points;

comparing the maximum depth with the tolerance limit of the worn surface;

determining a remanufacturing operation to be performed on the worn surface based on the comparison;

machining the worn surface beyond the tolerance limit of the worn surface if the maximum depth is greater than the tolerance limit; and     performing a material deposition operation on the machined surface.

11. The method of claim 10, wherein the worn surface defines a longitudinal axis and a transverse axis perpendicular to the longitudinal axis, and wherein the scanning device is moved along at least one of the longitudinal axis and the transverse axis.

12. The method of claim 10 further comprising removing a data point from the set of data points indicative of a depth greater than a predetermined threshold limit.

13. The method of claim 10 further comprising determining the position of the reference plane by reference to a reference point on the engine.

14. The method of claim 10 further comprising generating a three dimensional model of the worn surface based on the set of data points.

15. The method of claim 10, wherein the remanufacturing operation comprises machining the worn surface within the tolerance limit of the worn surface if the maximum depth is lesser than the tolerance limit.

16. The method of claim 10 further comprising, monitoring via a linear transducer, a position of the scanning device relative to the worn surface.

17. The method of claim 10, wherein the step of moving at least one of the scanning device and the worn surface includes rotating at least one of the scanning device and the worn surface about an axis.

18. A system for determining wear of a worn surface of an engine, the system comprising:

a support device disposed adjacent to the worn surface, the support device comprising an elongate member disposed at a distance relative to the worn surface, wherein the elongate member is movable relative to the worn surface;

a scanning device disposed on the elongate member of the support device, the scanning device configured to generate a set of data points, wherein each data point of the set of data points is indicative of a depth of a corresponding point on the worn surface relative to a reference plane; and     a controller disposed in communication with the scanning device, the controller configured to determine a maximum depth of the worn surface based on the set of data points and compare the maximum depth of the worn surface to a tolerance limit of the worn surface.

19. The system of claim 18, wherein the support device further comprises:

a first lateral member extending from a first end of the elongate member towards the worn surface;

a second lateral member extending from a second end of the elongate member towards the worn surface;

a stationary member disposed parallel to a longitudinal axis of the worn surface, wherein the first lateral member is slidably coupled to the stationary member; and     a linear transducer disposed on the second lateral member, the linear transducer configured to detect a position of the second lateral member relative to the worn surface.

* * * * *